United States Patent [19]

Yabe et al.

[11] Patent Number: 4,803,550
[45] Date of Patent: Feb. 7, 1989

[54] IMAGING APPARATUS HAVING ILLUMINATION MEANS

[75] Inventors: Hisao Yabe, Hachioji; Kenji Kimura, Tachikawa; Masahide Kanno, Hachioji; Kiyoshi Tsuji, Tana; Jun Yoshinaga, Hino; Takeshi Yokoi; Kazuhiko Ozeki, both of Hachioji; Shinichi Nishigaki, Tokyo; Takeaki Nakamura, Hino; Yoshikazu Tojo, Hachioji; Hiromasa Suzuki, Akishima, all of Japan

[73] Assignee: Olympus Optical Co., Ltd., Tokyo, Japan

[21] Appl. No.: 181,133

[22] Filed: Apr. 13, 1988

[30] Foreign Application Priority Data

Apr. 17, 1987 [JP] Japan ................... 62-94448
May 8, 1987 [JP] Japan ................... 62-112004
Oct. 7, 1987 [JP] Japan ................... 62-254068

[51] Int. Cl.$^4$ .................... A61B 1/04; A61B 1/06
[52] U.S. Cl. ............................ 358/98; 128/6; 358/228
[58] Field of Search ................. 358/98, 228; 128/6

[56] References Cited

U.S. PATENT DOCUMENTS 4,571,629 2/1986 Horio et al. .................. 358/225
4,729,018 3/1988 Watanabe .................... 358/98

FOREIGN PATENT DOCUMENTS 179129 8/1986 Japan .

Primary Examiner—Howard W. Britton

[57] ABSTRACT

An imaging apparatus for use in an electronic endoscope or the like is provided with a mechanically driven light-shielding plate, wherein imaging is effected by using a solid-state imaging device starting from a time when an amount of light shielded by this light-shielding plate becomes minimal, or imaging is effected repeatedly during a short exposure time within a transient period during which the amount of light shielded becomes minimal, and when an signal level of each image reaches a reference level, that signal is stored in a memory.

13 Claims, 12 Drawing Sheets

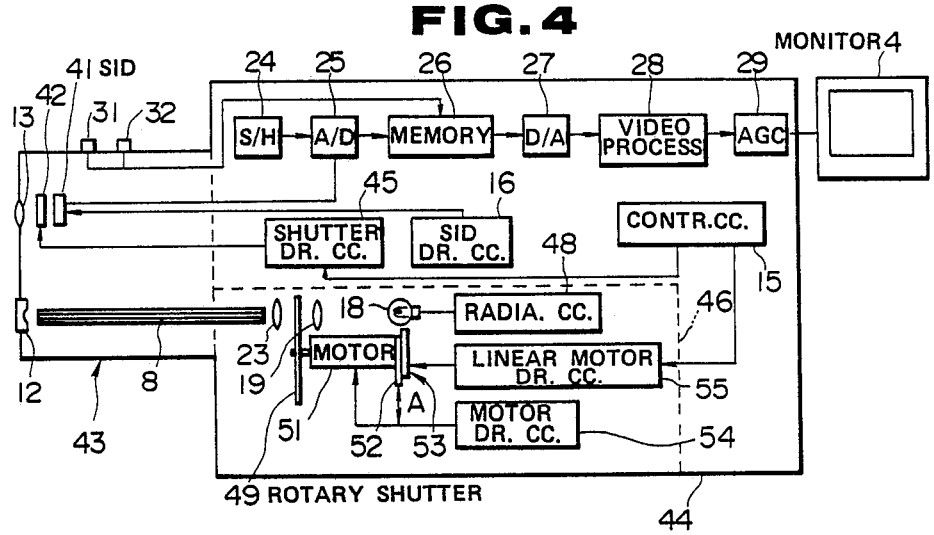
FIG. 4
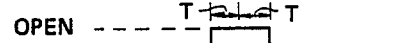
FIG. 6a EMISSION POWER FROM LG.
FIG. 6b READ-OUT TIMING OF SID
FIG. 6c SHUTTER OF LIQUID CRY.
FIG. 6d IMAGING FIELD
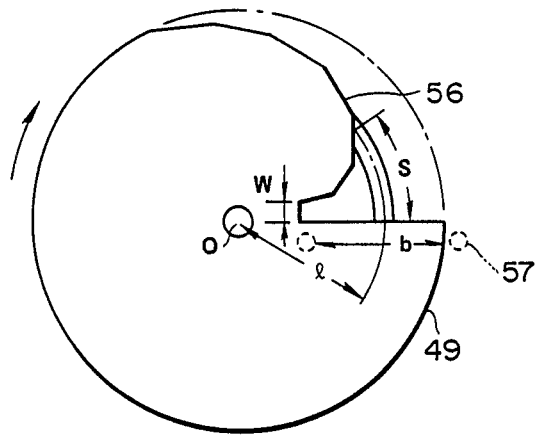
FIG. 5

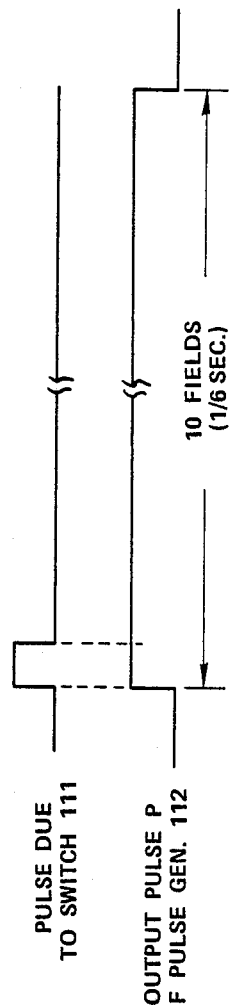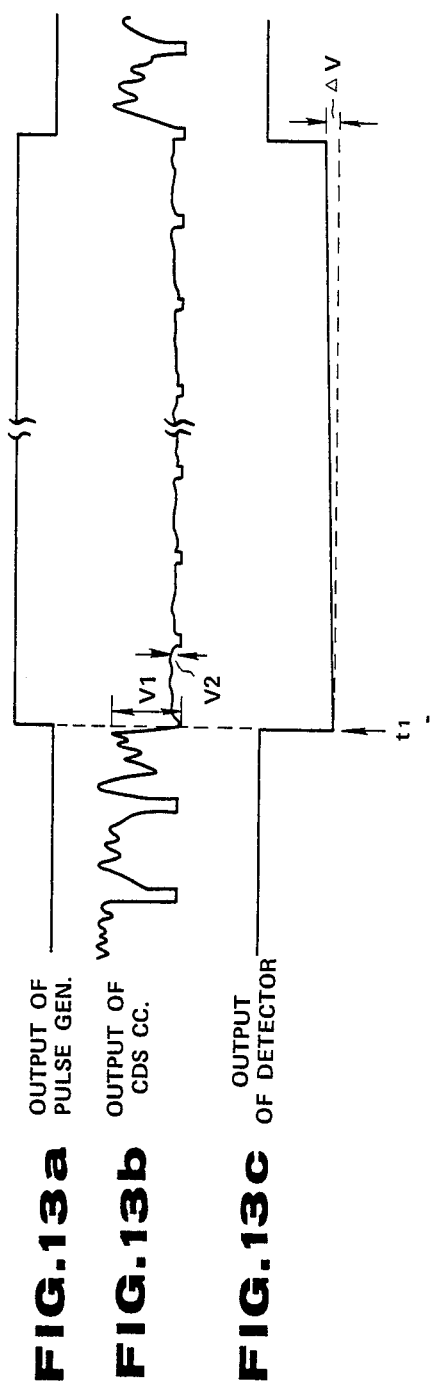

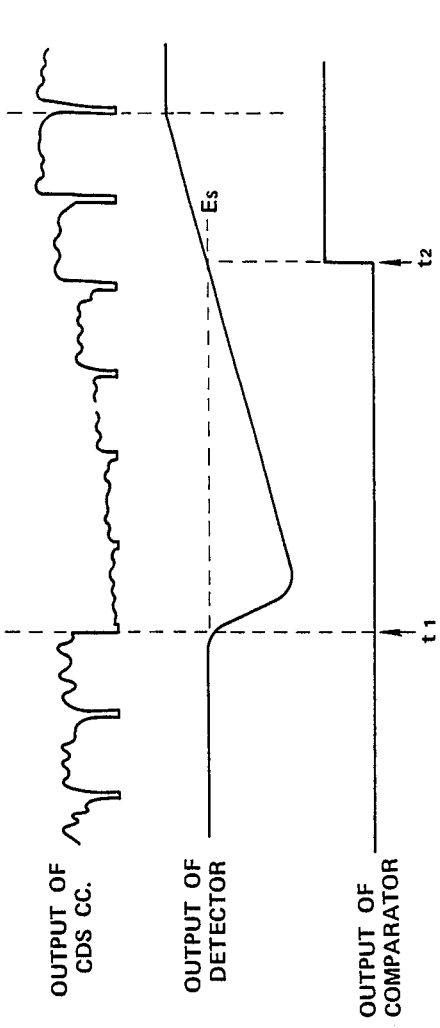
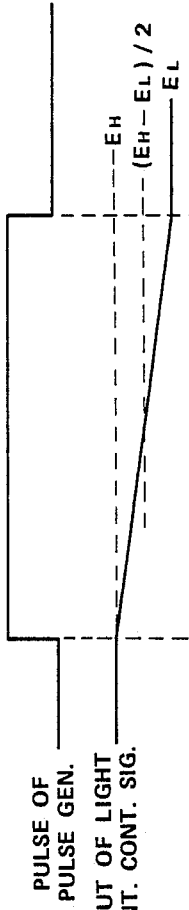
FIG.14a PULSE OF PULSE GEN.
FIG.14b OUTPUT OF LIGHT QUANT. CONT. SIG.
FIG.14c OUTPUT OF MIXER
FIG.15a OUTPUT OF MIXER
FIG.15b OUTPUT OF CDS CC.
FIG.15c OUTPUT OF DETECTOR
FIG.15e OUTPUT OF COMPARATOR

IMAGING APPARATUS HAVING ILLUMINATION MEANS

BACKGROUND OF THE INVENTION

Field of the Invention and Description of the Related Art

The present invention relates to an imaging apparatus having an illumination means.

Recently, electronic-type endoscopes (called electronic endoscopes or video endoscopes) in which solid-state imaging devices such as charge-coupled devices (hereafter abbreviated as CCDs) are used as imaging means have been put to practical use.

Since an imaging apparatus used in an endoscope is provided with an illumination means so as to shoot an image of an object in a dark place such as a somatic cavity, and imaging is effected under the illumination by the illumination means.

For instance, in the above-described endoscope, when examining the interior of a somatic cavity, an endoscopic image is set in a still mode to make a detailed observation, or a still image is recorded by a monitor imaging apparatus, an optical disk, or the like.

At that time, if an effective imaging period is long (e.g., 1/60 second), blurring occurs when the image is viewed as a still image. The shorter the distance between the tip of the endoscope and the wall of a somatic cavity (the distance of observation), the more this blurring is likely to occur.

As for this problem, as disclosed in U.S. Pat. No. 4,571,629, proposals have been made to shorten the effective imaging period to, for instance, 1/400 second or less by using a solid-state imaging device (hereafter referred to as the SID), thereby making it possible to prevent blurring.

In the prior art of aforementioned U.S. Pat. No. 4,571,629, a period of illumination is shortened by reducing the width of an opening provided in a rotary shutter so as to shorten the effective imaging period.

Incidentally, an element shutter is provided with a function (a reset function) in which charges accumulated in each pixel are not output as video signals and are extracted and discarded, and an interval between the reset and the read-out is set as required, thereby controlling the effective imaging period. As an example which is similar to this method, it is conceivable to provide an arrangement in which the SID itself is not provided with an element shutter, and a liquid crystal shutter is provided on the front of the SID, thereby shortening an exposure period (which is the effective imaging period in this case) with respect to the SID.

In the above-described U.S. Patent, the variable width of the opening can be set to only one half of the imaging period (1/60 second in the case of the NTSC system) at maximum, so that one half of the radiation power of the lamp is wasted. For that reason, if the distance of observation is long, there occurs trouble in which it becomes impossible to obtain an image of adequate brightness, such as a shortage in the amount of exposure of the SID.

Meanwhile, in the case of an electronic endoscope using an element shutter or a liquid crystal shutter, if a diagnosis is continued under strong illumination when the distance of observation is short, there occurs trouble due to thermic rays contained in the illumination, resulting in, for instance, a radiation burn, or thermal deformation or, in some cases, burning of an object in the case of an industrial camera. In this respect, no measure has been taken in the prior art.

Incidentally, there is an electronic endoscope which employs a method in which a mechanical diaphragm is detachably inserted at the front of a lamp. However, a shutter which operates at a high speed of 1/100 second or above cannot be realized, and the sound becomes disadvantageously large.

In addition, in an electronic endoscope in which a liquid crystal shutter is provided in front of the lamp, the liquid crystal shutter is liable to become damaged by the illumination light.

Furthermore, one using a flashing unit instead of a lamp has the drawbacks that the sound is large and anxiety is imparted to the patient.

Meanwhile, even if an attempt is made to shorten the charge-accumulating time, the signal-to-noise (S/N) ratio declines since the amount of charged accumulated also declines.

OBJECT AND SUMMARY OF THE INVENTION

Accordingly, it is an object of the present invention to provide an imaging apparatus having an illumination means which is capable of obtaining an image which is substantially free from blurring.

Another object of the present invention is to provide an imaging apparatus having an illumination means which is capable of obtaining an image with an excellent S/N ratio without causing a radiation burn.

Still another object of the present invention is to provide an imaging apparatus having an illumination means which is capable of obtaining an image with adequate brightness with respect to a wide range of distance of observation.

To these ends, according to the present invention, there is provided an imaging apparatus which is arranged such that, as a mechanical light-shielding member is moved rotatively in parallel, a quantity of illumination light to be applied to an object is set to a large level only during an effective imaging period by illumination light quantity controlling means, while the quantity of illumination light during periods other than that effective imaging period is set to a small level by the illumination light quantity controlling means, that imaging is effected during a short exposure time when the quantity of illumination light becomes large after the quantity of illumination light to be applied to the object is forcedly set to a large level, and that only an image shot at an appropriate level is stored, thereby obtaining an image which is substantially free from blurring and is provided with an appropriate degree of brightness.

The above and other objects, features and advantages of the present invention will become more apparent from the following detailed description of the invention when read in cojunction with the accompanying drawings.

BRIEF DESCRIPTION OF THE DRAWINGS

FIGS. 1 to 3 relate to a first embodiment of the present invention, in which

FIG. 1 is a schematic diagram of the first embodiment;

FIG. 2 is a schematic front elevational view of the first embodiment;

FIGS. 3a to 3g are diagrams illustrating the operation of the first embodiment;

FIG. 4 is a schematic diagram of a second embodiment of the present invention;

FIG. 5 is a front elevational view of a rotary shutter used in the second embodiment;

FIGS. 6a to 6d are diagrams illustrating the operation of the second embodiment;

FIGS. 7 to 16 relate to a third embodiment of the present invention, in which

FIG. 7 is a schematic diagram of a video endoscope in accordance with the third embodiment;

FIG. 8 is a schematic diagram of a video processing circuit;

FIG. 9 is a spectral diagram illustrating a signal band of a signal input to the video processing circuit;

FIG. 10 is a waveform diagram of a video signal input to the video processing circuit;

FIG. 11 is a diagram illustrating a light quantity adjusting member;

FIGS. 12a and 12b are diagrams illustrating that a pulse is output by the operation of a switch;

FIGS. 13a to 13c illustrating the operation of an automatic light-quantity adjusting member;

FIGS. 14a to 14c are diagrams illustrating a pulse of a pulse generator and an output waveform of a light quantity control signal for increasing a quantity of light output;

FIGS. 15a to 15e are timing charts illustrating the operation in a special imaging mode;

FIG. 16 is a schematic diagram of a CCD used in the third embodiment;

DESCRIPTION OF THE PREFERRED EMBODIMENTS

Referring now to the accompanying drawings, description will be made of the preferred embodiments of the present invention.

Figure 2:
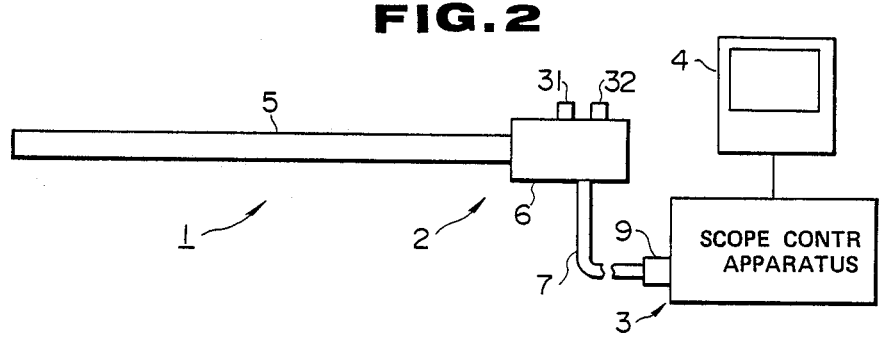

As shown in FIG. 2, an imaging apparatus 1 in accordance with a first embodiment comprises an endoscope body 2, an endoscope controlling apparatus 3 to which the endoscope body 2 is connected and which is provided with an illuminating means and a signal processing means, and a monitor 4 for displaying, as an image, video signals output from the (endoscope) controlling apparatus 3.

The endoscope body 2 has an elongated inserting section 5 which can be inserted into a somatic cavity or the like and a large-diameter operating section 6 connected to a rear end of the inserting section 5. A universal cord 7 extends from this operating section 6.

Figure 1:
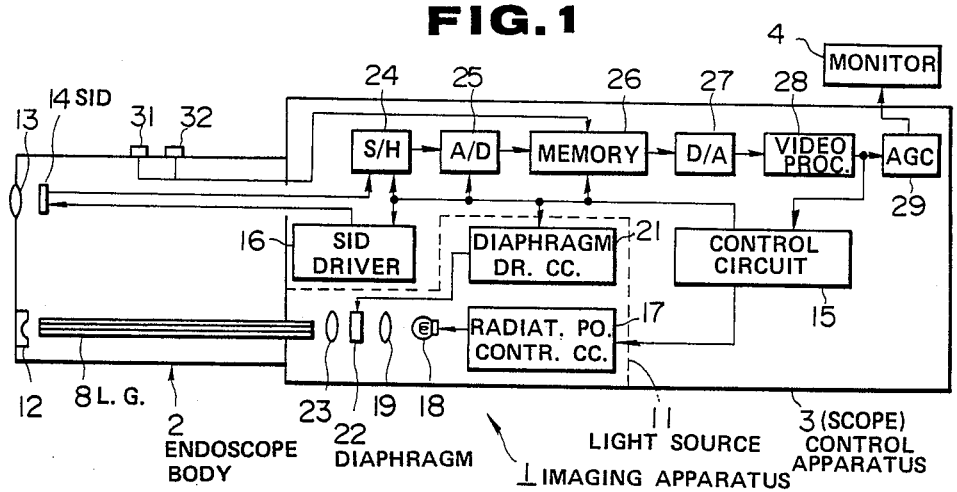

A light guide 8 which is constituted by a fiber bundle is inserted through the inserting section 5 and the universal cord 7 (as schematically shown in FIG. 1). A connector 9 of the universal cord 7 is connected to the control apparatus 3, illumination light from a light source 11 disposed inside the control apparatus 3 is condensed and radiated to an incident end surface of the light guide 8. Subsequently, the illumination light condensed and radiated to the incident end surface of the light guide 8 is transmitted through this light guide 8 and is made emergent in an expanding manner from an emergent end surface of the inserting section 5 on the tip side thereof via an illumination lens 12 so as to be radiated to an object.

Figure 3:
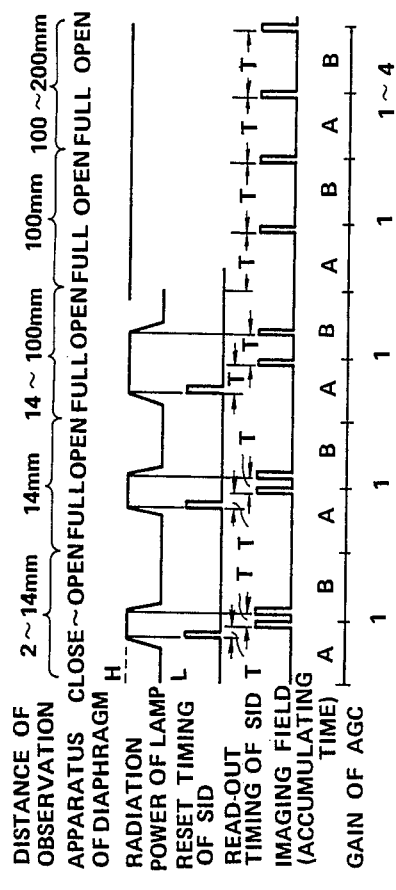

An optical image of the object illuminated with the above-described illumination light is formed on an imaging surface of a solid-state imaging device (SID) 14 such as a charge-coupled device (CCD), an MOS, a CMD (charge-modulating device), or the like by means of an objective lens. This SID 14 accumulates an amount of charges corresponding to the quantity of light received. In addition, a device having the function of an element shutter is used as the SID 14. In other words, a destructive reading-type SID is employed in which an SID drive circuit (or driver) 16 to which a command is applied from a control circuit 15 outputs a reset pulse, and the charges accummulated in the respective pixels of the SID 14 are made to disappear upon application of said reset pulse thereto. (Incidentally, when a non-destructive reading-type SID such as a CMD is used, it is necessary to effect a reset after a read-out upon completion of field A in FIG. 3.)

The light source 11 is arranged such that white light of a lamp 18 whose radiation power is controlled by a radiation power control circuit 17 is converted into a flux of parallel rays by a collimator lens 19, and, after the quantity of light is controlled via a diaphragm 22, the white light is then condensed and radiated to the incident end of the light guide 8.

An image signal which is output from the SID 14 by means of an SID drive signal output from the SID drive circuit 16 is sample-held by a sample-hold circuit 24 provided in the control apparatus 3. The signal sample-held by this sample-hold circuit 24 is converted into a digital signal from an analog signal by an A/D converter 25 and is then stored in a memory 26. The digital signal read out from the memory 26 is converted into an analog signal from a digital signal by means of a D/A converter 27, and is then input to a video processing circuit 28. Subsequently, this analog signal is converted into an NTSC composite video signal by the video processing circuit 28 and is displayed in color on the screen of the monitor 4 via an AGC circuit 29.

The output signal of the video processing circuit 28 is input to a control circuit 15. This control circuit 15 outputs a light-quantity adjustment signal to the radiation power control circuit 17 on the basis of a luminance component of the input signal so as to control the radiation power of the lamp 18. The controlling circuit 15 outputs a diaphragm control signal to a diaphragm drive circuit 21 on the basis of the luminance component, and a quantity of passing light is controlled by the diaphragm 22 to effect adjustment of the quantity of light.

The controlling circuit 15 also outputs a control signal to the SID drive circuit 16 to cause the same to effect adjustment of the quantity of light and also controls the sample-hold circuit 24, an A/D converter 25, and a memory 26 to output an image and a video signal having a period of 1/60 second.

In this first embodiment, as shown in FIG. 3f, one frame of 1/30 second consists of fields A and B, and control is effected in such a manner that an actual effective imaging time T in field A and that in field B become equal. In field A, the effective imaging time T spans between a reset timing shown in FIG. 3d and a read-out timing shown in FIG. 3e. In field B, as shown in FIG. 3e, the effective imaging time T spans between a read-out in field A and a read-out in field B. An output period (read-out period) of the SID 14 is 1/30 second in field A, but differs depending on the distance of observation in field B. Therefore, sample-holding is effected at a timing with a time lag of a fixed period from the read-out. Incidentally, since the effective imaging time T is set equal between field A and field B, the brightness of images in field A and field B becomes equal.

As shown in FIG. 3a, in an endoscope, the distance of observation is capable of varying by approximately 100 times within the range of 2 mm-200 mm, so that the light-quantity adjusting range is preferably the square of about 100-fold, i.e., 10,000-fold or thereabout. To realize this range, the effective imaging time T is variably controlled in accordance with the distance of observation, as shown in FIGS. 3d and 3e. For instance, this effective imaging time T is 1/60 second at maximum and 1/3,000 second at minimum, with the result that a 50-fold light-quantity adjusting range is provided in the range of 1/60–1/3,000 second.

Meanwhile, the diaphragm 22 for controlling the transmitted quantity of the illumination light of the lamp 18 is a mechanical diaphragm having a known structure, and is capable of varying the transmittance of the illumination light in the range of 2% to 100%. In other words, the light-quantity adjusting range of this diaphragm 22 is 50 times.

In addition, the AGC circuit 29 to which the NTSC image signal of the video processing circuit 28 is input is a circuit for setting the luminance level of the output signal to a fixed level (e.g., 0.35 V) without using the luminance level of the input signal. The AGC circuit 29 has a capacity of adjusting a 1-fold to 4-fold gain, as shown in FIG. 3g.

As for the total light-quantity adjusting range, 10,000 times is realized by the following: 50 times for the light-quantity adjusting range in the effective imaging time T of the SID 14, 50 times for the light-quantity adjusting range enabled by means of the diaphragm 22, and four times for the gain adjusting range enabled by the AGC circuit 29. Incidentally, the control circuit 15 controls the effective imaging time T of the SID and the amount of aperture of the diaphragm 22 so that the luminance level of the video process circuit 28 assumes a fixed value (0.35 V).

The lamp 18 in the light source 11 is, for example, a xenon lamp, and the radiation power of the xenon lamp is varied between a "H" (HI) level and an "L" (LO) level by the radiation power control circuit 17. The reason why the power is not turned ON and OFF is because the xenon lamp cannot be lit easily. In other words, the "L" level is set to such a brightness of a limit that does not cause the xenon lamp to go out.

As shown in FIG. 3c, the lamp 18 is set to the "H" level for a period of time slightly longer than the effective imaging times T of field A and field B, starting slightly before the effective imaging time T of field A and ending slightly after the effective imaging time T of field B, and is set to the "L" level elsewhere. An increase or decrease in the radiation power may take some time. In addition, after the radiation power is increased and the "H" level is reached, it takes some time until that level is stabilized. Therefore, an arrangement is provided such that the "H" level is reached slightly before the starting of the effective imaging time T in field A. For that reason, the radiation power is constantly fixed during the effective imaging time T, so that the adjustment of the light quantity is carried out very accurately.

Incidentally, an arrangement may be alternatively provided such that the effective imaging time T can be shortened to 1/3,000 second, but the period of the "H" level is not 1/1,500+α and cannot be set to, for instance, 1/400 second or less. The circuit of the radiation power control circuit 17 is thus simplified, and the radiation power at the "H" level is stabilized.

Incidentally, the endoscope body 2 is provided with a field freeze switch 31 and a frame freeze switch 32, and the memory 26 can be controlled by using these switches 31, 32.

For instance, if the field freeze switch 31 is depressed, the writing in the memory 26 is stopped, and the contents of field A are output to both fields A and B. Accordingly, an image on the monitor 4 becomes a still image.

Subsequently, if the field freeze switch 31 is depressed once again, freeze is canceled and the image becomes a moving image.

Meanwhile, if the frame freeze switch 32 is depressed, the writing in the memory 26 is stopped, and the contents of field A are output to field A, and the contents of field A to field B. Accordingly, the image on the monitor 4 becomes a still-freeze image as a result of freezing of field A.

If the frame freeze switch 32 is depressed once again, the freeze is cancelled, and the image is returned to the moving image.

Incidentally, if the frame freeze switch 32 is depressed during a field freeze, the mode is set in the frame freeze mode, while if the field freeze switch 31 is depressed during a frame freeze, the mode is set in the field freeze mode.

Since the effective imaging time T of field A and the effective imaging time T of field B are provided adjacent to each other, it is possible to obtain a still image which is substantially free from blurring during the frame freeze. Furthermore, since the changeover of the radiation power of the lamp between "H" and "L" can be effected only once for each frame, not once for each field, the configurations of the control circuit 15 and the radiation power control circuit 17 can be simplified.

Description will now be given of the operation of the first embodiment thus configured, with respect to how the light-quantity adjustment varies in accordance with the distance of observation D. (Incidentally, although FIGS. 3a to 3g illustrate how each function concerning light-quantity adjustment is performed at a certain timing, the axis of abscissas (time axis) is not actually continuous and is illustrated as being continuous for lack of space.)

(a) In the case of the distance of observation D: 14–100 mm

The diaphragm 22 is fully open, and the effective imaging time T varies within the range of 1/60–1/3,000 second in accordance with the distance. The output of the video processing circuit 28 is 0.35 V, and the gain of the AGC circuit 29 is 1. However, at a distance where D is close to 100 mm, and thereafter, the lamp 18 remains at the "H" level, and the effective imaging time T reaches 1/60 second in the vicinity of 100 mm.

(b) In the case of the distance of observation D: 100-200 mm

If the distance of observation D exceeds 100 mm, the diaphragm 22 is fully open, the lamp 18 is constantly set to the "H" level, the effective imaging time T is set to 1/60 second, and the output of the video processing circuit 28 falls below 0.35 V. Accordingly, the AGC circuit 29 increases the gain to set said output to an appropriate value, and the output of the AGC circuit 29 is thereby held at 0.35 V. In other words, when the distance D exceeds 100 mm, the brightness of the monitor 4 does not change, but the S/N ratio becomes deteriorated. In an endoscopic examination, if the distance exceeds 100 mm, it suffices in reality if only an orientation is established, so that an image with slightly deteriorated image quality is better than a dark image. If the distance D exceeds 200 mm, the capacity of the AGC circuit 29 is surpassed, so that the image on the monitor 4 becomes dark.

(c) In the case of the distance of observation D: 2-14 mm

When the distance of observation D is shorter than 25 mm or thereabout, the time duration of the "H" level of the lamp 18 is fixed to 1/400 second. In addition, when the distance D is 14 mm or less, the effective imaging time T becomes 1/3,000 second. When the distance D is 2-14 mm, the transmittance of the diaphragm 22 is set by the control circuit 15 and the diaphragm drive circuit 21. The outputs of the video processing circuit 28 and the AGC circuit 29 become 0.35 V.

When the distance D is shorter than 2 mm, since the light-quantity adjusting range is exceeded, the image on the monitor 4 becomes bright.

According to this first embodiment, an adequate light-quantity adjusting function is provided with respect to a wide range of distance, as described above.

In this first embodiment, the effective imaging time T is 1/60 second when the distance of observation D is 100 mm; 1/120 second when it is 70 mm; 1/750 second when it is 30 mm; and 1/3,000 second when it is 14 mm or less. When the distance D is long, blurring is unlikely to occur, so that it is possible to obtain still images which are virtually free from blurring with respect to all the distances D.

Furthermore, when the distance D is 14-25 mm, the time of the "H" level of the lamp 18 becomes 1/400 second. If the radiation power during the "L" level is assumed to be 1/5 of that obtained during the "H" level, the total quantity of illumination light becomes 27% of the quantity of light obtained during the "H" level alone. With this degree of light quantity, no radiation burn is caused to the object. Furthermore, since the transmittance of the diaphragm 22 is 25% when the distance D is 7 mm, the total quantity of illumination light is very small at 7% of that obtained during the "H" level alone. Accordingly, no radiation burn is caused to the object in all the distances of observation D.

Thus, in the first embodiment, since the quantity of illumination light is made sufficiently small during a period of time which starts slightly before and finishes slightly after the effective imaging time T, no radiation burn is caused to the object, and it is possible to obtain images which are virtually free from blurring.

Incidentally, in this first embodiment, if priorities of the light-quantity adjustment control are set in the order of the effective imaging time, the diaphragm, and the AGC, it is possible to obtain images which have the least amount of blurring and give the best S/N ratio.

In addition, there is an advantage in that the brightness of the image on the monitor 4 undergoes no change during a freeze if an arrangement is provided such that the effective imaging time is shortened not only during a freeze bit is constantly provided, and if the system of the light-quantity adjustment is not altered during the freeze. Moreover, there is an advantage in that no blurring occurs when the output of the control apparatus 3 is temporarily recorded on a VTR, and an output of the VTR is frozen.

It should be noted that the relationships between the distance of observation D and the effective imaging time T are not fixed, and since the F-number of an objective lens 13 and the quantity and length of the light guide 8 differ according to the types of the endoscope body 2, the relationships between the distance of observation D and the effective imaging time T may be varied in accordance with them. For instance, the brightness characteristics of such types of the endoscope body 2 may be classified into, say, four types, and the method of light-quantity adjustment may be varied in accordance with those classified types. For example, when a bright scope is used, an arrangement may be provided such that the effective imaging time T does not become longer than 1/240 second.

Furthermore, during a freeze, the radiation power of the lamp 18 may be fixed at the "L" level. With this arrangement, a radiation burn is unlikely to occur even if the distance of observation D becomes short during a freeze.

In this embodiment, the radiation power of the lamp 18 is set to two levels, "H" and "L"; however, the "H" level may be made variable, and may be used as an element of light-quantity adjustment. In this embodiment, two levels are used to simplify the configuration of the radiation power control circuit 17.

In the above-described first embodiment, the SID 14 is provided with the function of an element shutter. In a second embodiment of the present invention illustrated in FIG. 4, an SID 41 which does not have the function of the element shutter is used. An endoscope body 43 provided with a solid shutter 42, such as a liquid crystal shutter, is used in the front of the SID 41. Incidentally, the SID 41 and the solid shutter 42 may be formed into a single element.

The opening and closing operations of the above-described shutter 42 are effected by a shutter drive circuit 45 disposed inside the control apparatus 44. This shutter drive circuit 45 is controlled by the control circuit 15.

In this embodiment, radiation by the lamp 18 in a light source 46 is controlled by a radiation circuit 48.

In addition, in this embodiment, a rotary shutter 49 shown in FIG. 5 is used instead of the diaphragm 22 of the first embodiment. This rotary shutter 49 is rotatively driven by a motor 51. Furthermore, this rotary shutter 49 is so arranged as to be capable of being moved together with the motor 51 by a linear motor 53 whose movable portion 52 is movable in the direction of the arrow A relative to a stator.

The aforementioned motor 51 and linear motor 53 are respectively controlled by a motor drive circuit 54 and a linear motor drive circuit 55. Incidentally, the linear motor drive circuit 55 is controlled by the control circuit 15.

The other arrangements are the same as those of the first embodiment, and the same elements are denoted by the same reference numerals.

As shown in FIG. 5, a notch 56 is formed in the rotary shutter 49 in such a manner that a peripheral portion of a light-shielding disk is notched in a spiral shape. The arrangement is such that the period of shutter opening can be varied continuously by means of the notch 56 as the rotary shutter 49 is rotated around the rotational center 0 thereof. For instance, in FIG. 5, a small circle 57 indicates the size of a light beam, and when the distance between the light beam and the rotational center 0 is l, a period corresponding to the length of an arc S is the period when the shutter is open.

The rotary shutter 49 rotates at a rate of 30 revolutions per second, which coincides with the period of one frame of a video signal of the NTSC system.

As the rotational center 0 of the rotary shutter 49 is moved by the linear motor 53, the light beam 57 relatively moves within the range of b shown in FIG. 5.

When the light beam 57 faces a notch 56 in the rotary shutter 49, illumination light is radiated to the incident end surface of the light guide 8, the illumination light which is radiated to this light guide 8 is made emergent from the tip surface of the light guide 8 toward the object. The quantity of light which is radiated to the incident end surface of the light guide 8 or is made emergent from the tip surface of the light guide 8 is shown in FIG. 6a.

Since the above-described shutter 49 is used, a quantity of emergent light such as the one shown in FIG. 6a is obtained. As shown in FIG. 6b, a read-out timing of the SID in field A is set in synchronism with a substantially central time of the period when the rotary shutter 49 is open. Incidentally, in the case of field A, the effective imaging time T spans between the time when the liquid crystal shutter 42 opens (the rotary shutter 49 opens before the liquid crystal shutter 42 opens) and the time when a read-out is carried out. Meanwhile, in the case of field B, the effective imaging time T spans between the time when the read-out of field A is completed and the time when the liquid crystal shutter 42 is closed.

As shown in FIG. 6c, control is effected in such a manner that the liquid crystal shutter 42 is open for a time duration starting shortly before and ending shortly after the timing when the read-out of field A is carried out, i.e., for a period of 2T.

The rotary shutter 49 is open for a period of a time which starts immediately before the moment when the liquid crystal shutter 42 opens and finishes after the shutter 42 has closed again, as shown in FIG. 6c. The transmittance of the quantity of illumination light transmitted through the rotary shutter 49 when the rotary shutter 49 is open is 100%. (Since the transmittance becomes 100% unlike the case of the aforementioned U.S. Patent, there is no loss in the quantity of light.)

In addition, in terms of the arrangement, the fibers of the light guide 8 at the incident end thereof are substantially aligned with those at the emergent end thereof. If the quantity of illumination light is cut by the rotary shutter 49, an effect is exerted on the distribution of light at the incident end of the light guide 8. In other words, in a state in which part of the light beam 47 is cut by the rotary shutter 49, the distribution of illumination light made emergent from the illumination lens 12 becomes deteriorated. In this embodiment, however, imaging is not carried out in the state in which part thereof is cut, so that such a fault does not occur.

This embodiment produces effects that are similar to those of the first embodiment. In addition, in this embodiment, the control circuit 15 needs to control only the shutter drive circuit 45 and the linear motor drive circuit 55. Hence, the arrangements of the control circuit 15, the SID drive circuit 16, the sample-hold circuit 24, the A/D converter 25, and the radiation circuit 48 can be made simpler than those of the first embodiment.

Incidentally, in industrial applications, a pickup tube may be used instead of the SID 41.

In the foregoing embodiments, an electronic endoscope of a type in which the SID 14 or 41 is incorporated in a distal end portion of the inserting section is illustrated. However, the present invention is not restricted to this type alone, and can be similarly applied to a type having a television camera with the SID 14 or 41 incorporated in the eyepiece section of a fiberscope.

As has been described above, in accordance with the first and second embodiments, the quantity of illumination light is increased during the effective imaging time during which imaging is actually carried out by imaging means, and the quantity of illumination light is reduced during a period other than the effective imaging time as well as short time durations immediately preceding and following that time. Accordingly, the risk of causing a radiation burn or the like to the object can be overcome, and the length of the effective imaging time can be varied in accordance with the distance of observation or the like, so that an image of an appropriate brightness can be obtained.

Figure 7:
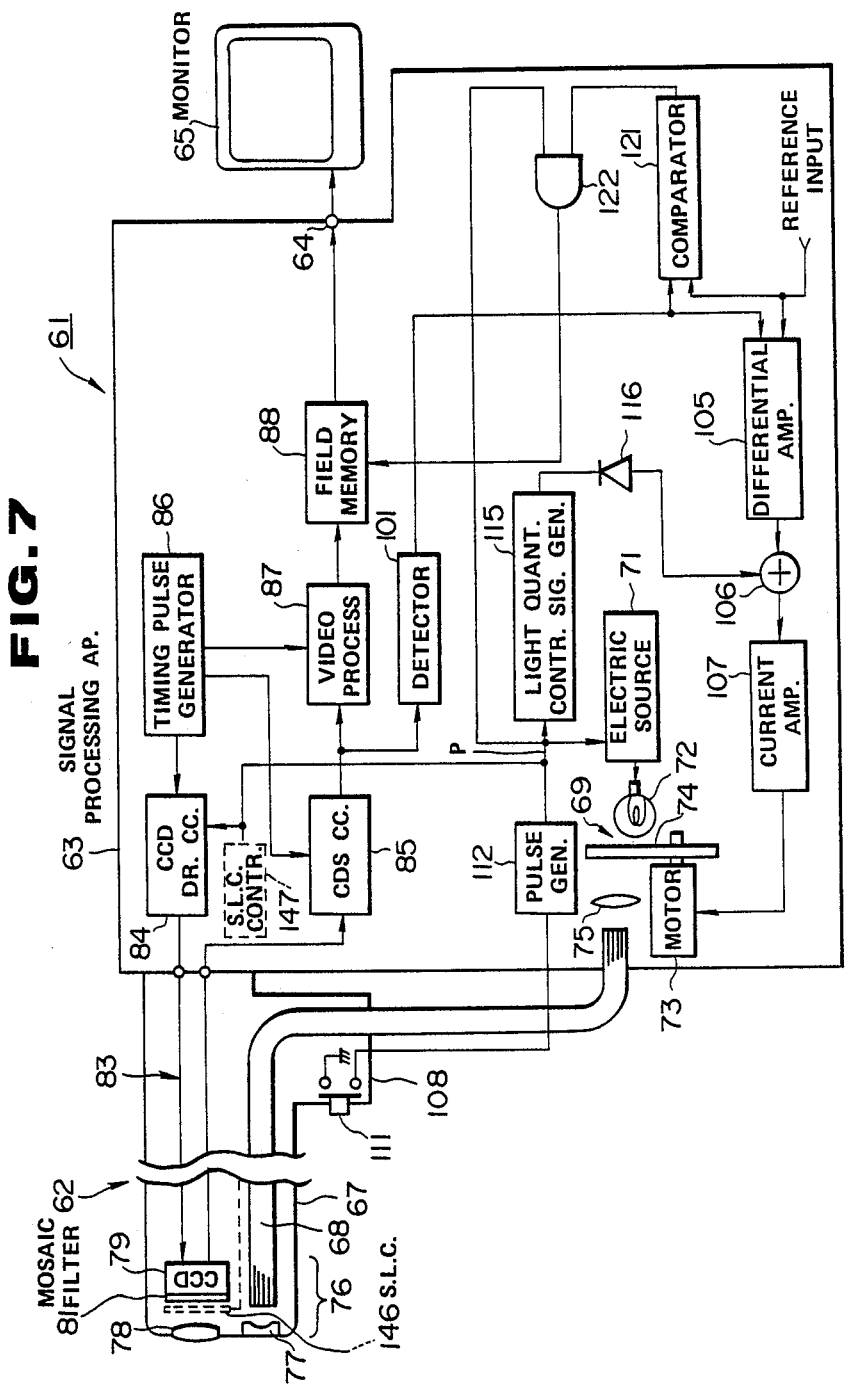

As shown in FIG. 7, a video endoscope apparatus 61 serving as an imaging apparatus in accordance with a third embodiment of the present invention comprises a video endoscope (body) 62, a signal processor 63 incorporating a signal processing means and a light source means for the video endoscope 62, and a color monitor 65 for displaying a video signal output from an output terminal 64 of the signal processor 63.

The video endoscope 62 has an elongated inserting section 67 which is adapted to be inserted into a somatic cavity or the like. A light guide 68 for transmitting illumination is inserted into this inserting section 67, and illumination light is supplied as an incident end surface of the light guide 68 is connected to a connector receptacle of a light source 69.

The light source 69 is so arranged that white light from a white lamp 72 such as a xenon lamp which is lit by electricity supplied from a power source 71 is passed through a light-quantity adjusting member 74 which is rotatable by a motor 73 so as to make it possible to vary a quantity of light to be transmitted. The white light transmitted through this light-quantity adjusting member 74 is condensed by a condenser lens 75 and is radiated to an incident end surface of the light guide 68.

The illumination light transmitted through the light guide 68 is made emergent from an emergent end surface of a distal end portion 76 of the inserting section 67 so as to be radiated to the object via a light distribution lens 77. Subsequently, an image of the illuminated object is formed by an objective lens 78 on a CCD 79 which is disposed on the focal plane thereof. Incidentally, a complementary-color mosaic filter (a complementary-color filter arranged in the form of a mosaic) 81 is installed on a light-receiving surface (imaging surface) of this CCD 79.

In the CCD 79, as a horizontal transmission pulse $\phi H$, a reset pulse $\phi R$, and a vertical transmission pulse $\phi V$ are applied from a CCD drive circuit 84 via a signal cable group 83, a photoelectrically converted signal is output and is then transmitted by the signal cable group 83 as to be input to a correlational double sampling circuit 25 (hereafter abbreviated as the CDS circuit). Subsequently, the signal is double-sampled, and 1/f noise and the like generated from the CCD 79 is inhibited. A sampling pulse of this CDS circuit 25 is supplied from a timing pulse generator 86, and sampling is effected for each unit of the pixel. An output of this CDS circuit 25 is input to a video processing circuit 87 where it is converted into, for instance, a NTSC composite video signal, and is input to a field memory 88.

Figure 8:
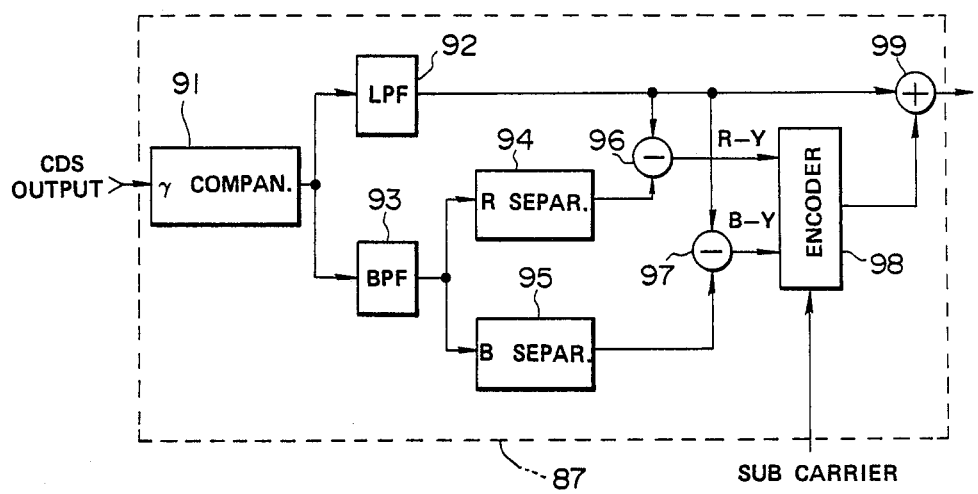

A specific configuration of the aforementioned video processing circuit 87 is shown in FIG. 8.

The output signal of the CDS circuit 85 includes a component of a luminance signal and a component of a chrominance signal. This CDS output signal is input to a γ-compensation circuit 91, and after γ-characteristics are substantially converted into 0.45, the signal is input to a low-pass filter (hereafter abbreviated as the LPF) 92 and a band-pass filter (hereafter abbreviated as the BPF) 93. In this embodiment, the complementary-color mosaic filter (e.g., the MN8232R manufactured by Matsushita Electric Industry Co., Ltd.) 81 is used. Accordingly, in this CCD 79, a luminance signal is generated in a base band, and a chrominance signal is obtained as a carrier.

Figure 9:
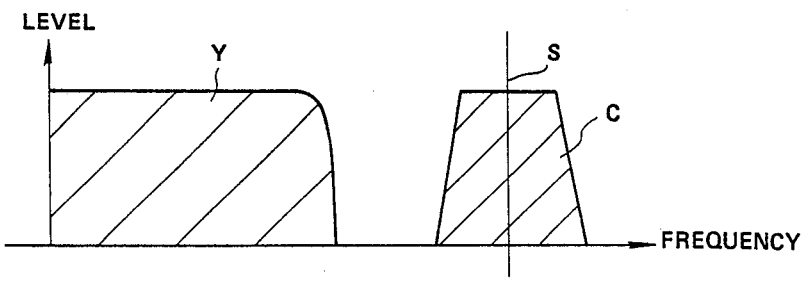

FIG. 9 is a spectral diagram of an output signal of the CCD 79, in which Y denotes the component of the luminance signal which is obtained as the base band, S denotes a carrier source for carrying the component of the chrominance signal, and C denotes the chrominance signal. The luminance signal is separated and extracted by the LPF 92 which cuts off frequencies between the bands of the two signals Y and C. Meanwhile, S and C (chrominance carrier) are separated and extracted by the BPF 93 in which the aforementioned chrominance signal band is set as a passband.

With respect to the chrominance carrier separated by the BPF 93, an R signal (red signal) is separated by an R separator 94, and a B signal (blue signal) is separated and extracted by a B separator 95. The chrominance signals thus separated by the R and B separators 94, 95 are respectively input to differential circuits (subtraction circuits) 96 and 97, and the luminance signals Y are then input to both of the differential circuits 96, 97, respectively, where these luminance signals Y are subtracted. As a result, color-difference signals R-Y, B-Y are output.

These two color-difference signals R-Y, B-Y are input to a color encoder circuit 98 and are used as an input for modulation by a quadrature modulator using a subcarrier. An output of this color encoder circuit 98 serves as a chrominance signal, is input to one terminal of a mixer 39, and is mixed with the luminance signal Y which is input to the other terminal of the mixer 39, so as to be output as, for instance, an NTSC composite video signal.

The output signal of the CDS circuit 25 shown in FIG. 7 is input to the aforementioned video processing circuit 27 and is also input to a detector 101, where the signal is detected at the level of an average or peak value and is converted into a DC signal. The selection of the average value or the peak value can be made arbitrarily according to the conditions of the object. In this embodiment, however, average-value detection is adopted. As a result, a DC signal of the magnitude which is proportional to the output level of photoelectric conversion by the CCD 79 is generated.

Figure 10:

For instance, the solid line in FIG. 10 represents a signal which is output from the CDS circuit 85, while the dotted line represents a DC voltage level 102 detected at the average value, this DC voltage level 102 being used as a signal which is output from the detector 101. Incidentally, $E_O$ indicates the lowest level. The output level of the detector 101 naturally varies in response to the output level of photoelectric conversion by the CCD 79.

The output level of photoelectric conversion by the CCD 79 also varies in response to the intensity of illumination. A means for increasing the quantity of illumination light by using the light-quantity adjusting member 74 shown in FIG. 11 is provided in this embodiment.

Figure 11:
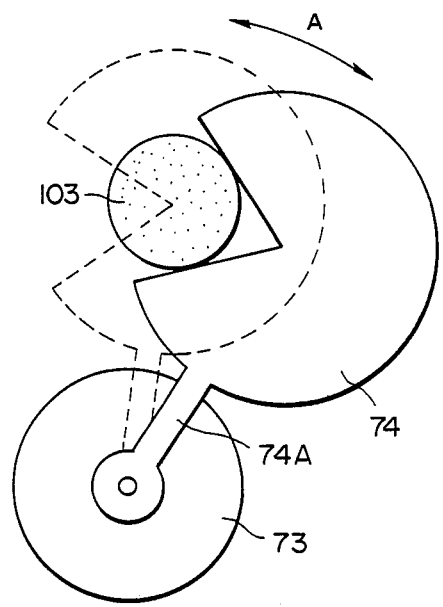

FIG. 11 is a schematic diagram of a peripheral portion of the light-quantity adjusting member 74 as viewed in the direction of the axis of illumination light.

The light-quantity adjusting member 74 has an arm 74A which is installed on a rotational shaft of the motor 73 and is adapted to be rotatable in either of the directions indicated by the arrows A in response to the direction of the rotation of the motor 73. A disk-shaped light-shielding portion of the light-quantity adjusting member 74 is provided with a notch, and part of a light beam 103 facing this notch advances toward the condenser lens 75, while the remaining portion of the light beam 103 facing the portion of the light-shielding portion other than the notch is shielded from light.

For instance, the state shown by the solid line in FIG. 11 is a fully open state in which substantially all of the light beam 103 is transmitted. Meanwhile, the state shown by the dotted line is a state in which the quantity of illumination light is restrained substantially. Thus, since the rotation of the light-quantity adjusting member 74 is controlled such as to be reversible, it is possible to adjust the quantity of illumination light to be applied to the object. Incidentally, as will be described later, in the normal shooting mode, adjustment of the light quantity by the light-quantity adjusting member 74 is automatically controlled, and the light-quantity adjusting member 74 is generally held in a state in which it is not fully open. In a special shooting mode in which shooting is effected within a short period of time, light-quantity adjustment is carried out in such a manner that the light-quantity adjusting member 74 is gradually opened in the fully opening direction. The arrangement is such that determination is made as to whether or not the level of the signal of the image shot at that time has reached a predetermined level, and when that predetermined level has been reached, that shooting signal is held in the field memory 88.

The output signal of the detector 101 is applied to one input terminal of the differential amplifier 105, while a reference voltage $E_S$ is applied to the other input terminal thereof. The voltage value of this reference voltage $E_S$ is set to a voltage which is substantially equivalent to the output level of the detector 101 obtained at the time when the output of the video signal becomes an appropriate level. Namely, this reference voltage $E_S$ serves as a reference level for the automatic light-quantity adjustment. The output of this differential amplifier 105 is input to a current amplifier 107 via a mixer 106, and is subjected to current amplification so as to drive the DC reversible motor 73. A control loop for effecting automatic light-quantity adjustment is thus configured, and the amount of rotation of the light-quantity adjusting member 74 is reversibly controlled in such a manner that the output voltage of the detector 101 becomes equivalent to the reference voltage $E_S$ by means of this control loop of the automatic light-quantity adjustment.

The operating section 108 of the above-described endoscope 62 is provided with a switch 111 for a special shooting mode for shooting an image by effecting a changeover, for instance, from the normal accumulating time of 1/60 second (exposure time) to the accumulating time of 1/10 thereof, i.e., 1/600 second. When this switch 111 is turned ON, a trigger signal is input to a pulse generator 112, and a pulse is output, beginning at the point of time when the switch 111 is depressed.

In this embodiment, a pulse generator 112 is adapted to output the pulse P over a period of 10 fields (i.e., 1/6 second), as shown in FIG. 12b, by means of a triggering pulse which is output when the switch 111 is depressed, as shown in FIG. 12a.

The output pulse P of the pulse generator 112 is input to the CCD drive circuit 84, and when this pulse P is at "H", the drive circuit 84 sets the read-out period to 1/10 of the normal period and reads out accumulated signals from the CCD 79. Incidentally, since the above-described control means of automatic light-quantity adjustment is provided in this embodiment, if the mode is set to the special shooting mode by depressing the switch 111, the accumulation time becomes 1/10 of the normal time, so that the output level of the CCD 79 becomes approximately 1/10, so that the light-quantity adjusting member 74 is rotated in the fully opening direction by virtue of the automatic light-quantity adjusting function.

However, it takes time in following up the control of this automatic light-quantity adjustment, and a follow-up time of approximately two seconds is required in reality. For this reason, in the period of the aforementioned 10 fields or thereabout, the output of the CDS circuit 85 at the time when the means of controlling the automatic light-quantity adjustment is used is shown in FIG. 13.

In other words, in the normal shooting mode during the time illustrated on the left-hand side of FIG. 13, the output signal of the CDS circuit 85 is at an appropriate level, and the switch 111 is turned ON at a timing indicated by t1, and the pulse P is output from a pulse generator 112, as shown in FIG. 13a. At the same time, the output of photoelectric conversion is lowered to 1/10 of the normal level. Hence, as shown in FIG. 13b, as compared with the previous signal level (indicated by V1) prior to the timing t1, the output signal of the CDS circuit 85 drops to approximately 1/10 (indicated by V2) of that signal level during a period when the pulse P is being output subsequently to the timing t1. Control of the automatic light-quantity adjustment does not follow up instantly, as described above, and the output of the detector 101 rises gradually by the automatic light-quantity adjustment, as shown in FIG. 13c. In 1/6 second or thereabout, however, this output rises only slightly (the value of this rise is indicated by $\Delta V$ in FIG. 13c).

For this reason, in this embodiment, the following means is provided to ensure that a frozen image which is substantially free from blurring can be obtained even in 1/6 second or thereabout.

The output of the pulse generator 112 is input to a light quantity control signal generator 115 where a single sawtooth wave (a slope wave) is generated. This sawtooth wave is input to the other input terminal of the mixer 106 via a diode 116, and is superposed on the output signal of the aforementioned differential amplifier 105 so as to be input to the current amplifier 107. The motor 73 is driven by this sawtooth wave to forcedly open the light-quantity adjusting member 74, thereby increasing the quantity of illumination light.

Upon being triggered by the pulse P generated by the pulse generator 112, as shown in FIG. 14a, the light quantity control signal generator 115 outputs a sawtooth wave, as shown in FIG. 14b. As for the voltage value of this sawtooth wave, its initial value $E_H$ is higher than a maximum value of the output voltage of the differential amplifier 105, while a final minimum value $E_L$ of the sawtooth wave is set to such a level that exceeds a minimum output value of the detector 101. The generated sawtooth wave is mixed with the output of the differential amplifier 105 via the diode 116, and the mixed waveform is shown in FIG. 14c. In this drawing, reference character $E_R$ denotes an output voltage of the differential amplifier 105 at the time when the automatic light-quality adjustment is being made. When the pulse P is output, the sawtooth wave is superposed on this voltage, and a voltage waveform which declines in the form of a slope is obtained. Ultimately, the output voltage of the differential amplifier 105 becomes $E_{RL}$, whereupon the light-quantity adjusting member 74 assumes a state in which the light beam is not shielded at all, i.e., the fully open state shown by the solid line in FIG. 11. For this reason, the light beam radiated to the object becomes maximum. On the contrary, at a voltage which is higher than $E_R$, the light-quantity adjusting member 74 is moved to the position at which the light beam is shielded completely. In addition, a mean potential ($E_H - E_L$) of the sawtooth wave in FIG. 14b is set such as to be substantially equivalent to the voltage $E_R$ for operating the automatic light-quantity adjustment. Incidentally, the diode 116 serves to prevent the initial value $E_H$ of the sawtooth wave from exerting an influence on the output $E_R$ of the differential amplifier 105. The potential of $E_R$ varies every moment in accordance with the conditions of the object, so that $E_H$ and $E_L$ are made wider than the output range of the differential amplifier 45. Since this arrangement is adopted, simultaneously as the accumulation time is changed over from 1/60 second to 1/600 second, the quantity of emergent light changes toward the maximum value by following up the control voltage shown in FIG. 14c. Subsequently, when the average level of the input signals detected by the detector 101 while the quantity of emergent light is increasing toward the maximum quantity of emergent light, the video signal of an image shot in the next field is written in the field memory 88 so as to obtain a frozen image in the special shooting mode.

For this reason, the output signal of the detector 101 is input to one input terminal of a comparator 121, while the reference voltage $E_S$ corresponding to an appropriate level is applied to the other input terminal thereof. An output of comparison obtained when this appropriate level is reached is input to one input terminal of an AND circuit 122. Meanwhile, the output of the pulse generator 112 is applied to the other input terminal of the AND circuit 122, and this AND gate is opened by the pulse of the pulse generator 112. In this open state, when a signal is output from the comparator 121 (indicating that the output of the detector 101 has reached an appropriate level), that output passes through the AND gate and is applied to a write controlling terminal of the field memory 88, where one field of a composite video signal which is output from the video processing circuit 87 during the next field, is stored.

Referring now to FIG. 15, a description will be given of the above-described operation.

For instance, when the mode is to be changed over to the special shooting mode at a timing ti, the light-quantity control signal generator 115 outputs a sawtooth wave, which is added to a normal automatic light-quantity adjustment signal by the mixer 106 so as to provide a signal of the waveform shown in FIG. 15a. This signal drives the motor 73 via the current amplifier 107, and rotates the light-quantity adjusting member 74 in the direction of forcedly fully opening the same, thereby increasing the quantity of illumination light.

Accordingly, the output of the CDS circuit 25 practically drops to an output level of about 1/10 at the timing t1, as shown in FIG. 15b, and the light-quantity adjusting member 74 is then forcedly caused to retreat from the optical path. Therefore, the output level increases gradually with an increase of the quantity of emergent light corresponding to that retreat.

In addition, with respect to the output of the detector 101 as well, as shown in FIG. 15, an average output level thereof drops to about 1/10 immediately after the timing t1, but the output of its mean value also increases with an increase in the quantity of light by the light-quantity adjusting member 74. The output of the comparator 121 to which the output of this detector 101 is input is initially "0", as shown in FIG. 15d, and at a timing t2 when the output level of the detector 101 reaches the level of the reference voltage $E_S$, the output of the comparator 121 is changed over to "1". Consequently, this output is applied to the field memory 88 via the AND gate. Hence, the next one-field portion of the video signal is stored in the field memory 88, and this stored video signal can be displayed on the color monitor 65 as a frozen image.

According to this embodiment, it is possible to obtain frozen video image signals which have a high S/N ratio and are substantially free from blurring. In addition, there is also an advantage in that it is possible to obtain such signals with a simple arrangement and without enlarging the external configuration of the video endoscope 62. Furthermore, this embodiment can also be applied to a conventional video endoscope by altering a signal processing system.

It should be noted that, in this embodiment, for instance, a xenon lamp is used as the light source lamp 72, and it is possible to increase the radiation power by instantly increasing a voltage to be applied to this lamp (flashing) and without sacrificing the life of the lamp. Incidentally, the output pulse of the pulse generator 112 is also input to the power source 71, a lack of sensitivity of the CCD 71 in a case where the accumulation time is shifted to 1/600 second in the 1/6-second special shooting mode is compensated on the light source side.

Figure 16A:
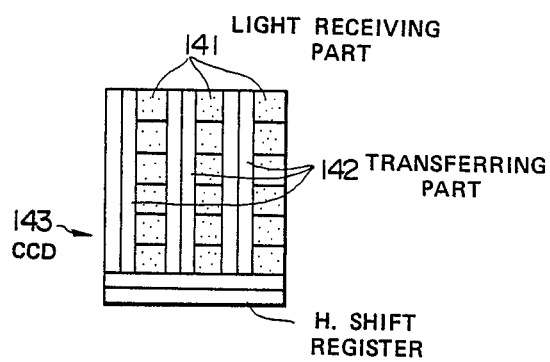
Figure 16B:
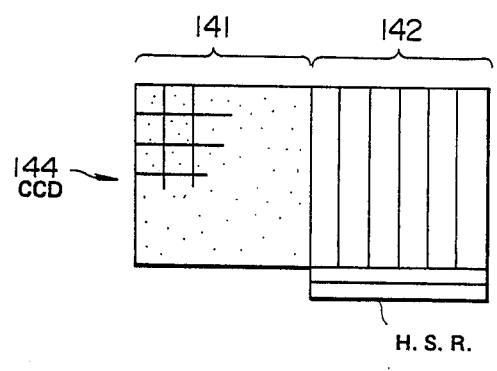
Figure 16C:
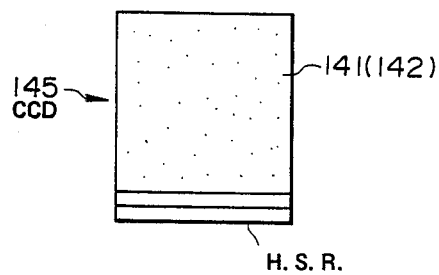

Incidentally, as for the CCD 71, it is possible to use a CCD 143 of a frame transfer type in which a light-receiving part 141 and a transferring part 142 are not common, or a CCD 144 of an interline transfer type, as respectively shown in FIGS. 16a and 16b. When the CCD 143 or 144 is used, in the case of the special shooting mode, the signal charge of the light receiving part 141 is transferred to the transferring part 142 immediately before the drive signal is applied, and the signal charge is read out from this transferring part 142. If this arrangement is adopted, the phenomenon of smear can be prevented during a read-out. Meanwhile, in the case of a CCD 145 of a line transfer type in which the light-receiving part also functions as the transferring part, as shown in FIG. 16c, an arrangement may be provided such that a liquid crystal shutter 146 is arranged, as shown by a dotted line in FIG. 7, and that, during application of a drive signal, this liquid crystal shutter 146 is maintained in a light-shielding state by means of a liquid crystal shutter control means 147 so as to prevent the occurrence of the phenomenon of smearing.

Also, an arrangement may be provided such that, during the special shooting mode, a light source lamp for the special shooting mode is made to flash, that the quantity of light is increased in stages, and that, when a signal level which is output from the detector 101 during that flashing is at an appropriate level, the signal is stored in the field memory 88. In this case, an arrangement can be provided such that when that appropriate level is detected, the mode is returned to the usual shooting mode upon completion of accumulation of one field of charges. In addition, an arrangement may also be provided such that the flashing is maintained at a level for obtaining the appropriate level, and the output signal of the detector 101 is output to an optical storing means or the like so as to effect high-speed imaging.

Furthermore, when performing flashing on the light source side, if radiation is effected by variably controlling the intensity of radiation by means of detecting the level of the quantity of illumination light immediately before the special shooting mode so that the intensity of radiation will become approximately 10-fold that quantity of illumination light (when the accumulation of charges is effected on the basis of 1/10), it is possible to obtain a video signal which has a sufficiently high S/N ratio and is free of blurring of images, even if the signal is stored in the field memory or the like without necessarily making a judgment as to whether or not the output level of the detector 101 is at an appropriate level.

Incidentally, it is apparent that the present invention is also applicable to a video endoscope apparatus provided with a television camera in which, as an imaging means, a solid-state imaging device is employed in an eyepiece section of an optical scope.

Although, in FIG. 7, the quantity of light being transmitted is made variable by forwardly or reversely rotating the light-quantity adjusting member 74 by means of the motor 73, it also suffices to adopt the arrangement in which the rotary shutter 49 is rotated in one direction, as shown in FIG. 4 or 5.

Also, an apparatus is known in which a photographic device is mounted on a monitor for displaying an endoscopic image so as to allow the endoscopic image to be photographed.

Since the aspect ratio of the display screen of the monitor just mentioned differs from that of a 35 mm film, there have been cases where data displayed on the display screen in the prior art are not fully covered in a photographed film, and where, when necessary data are photographed, the screen frame of the monitor is included in the photograph. Thus, it has been impossible to effect display appropriate for photography.

Figure 17:
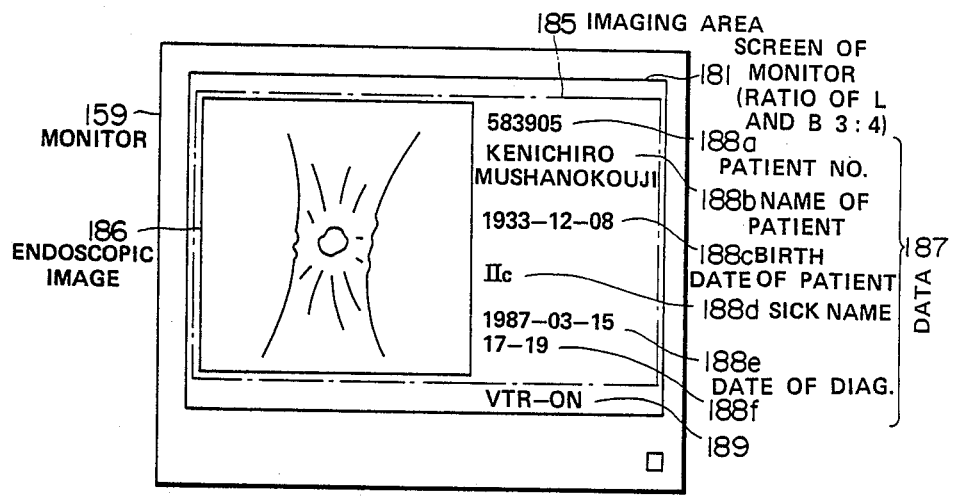
FIG. 17 is a digram illustrating a manner in which an endoscopic image and data are displayed on a monitor screen.

For this reason, as shown in FIG. 17, an arrangement may be provided such that the display of an endoscopic image and data is effected by a method appropriate for photography.

Figure 18:
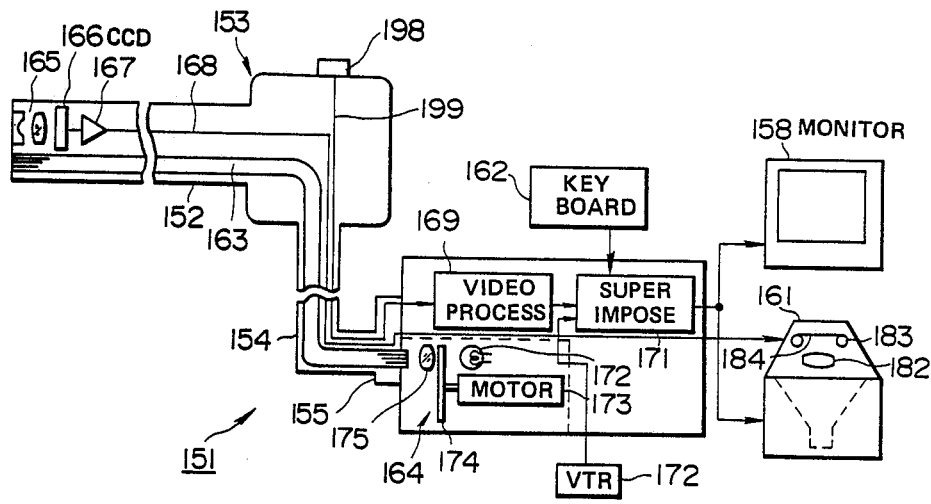
FIG. 18 is a schematic diagram of an endoscope for effecting the display shown in FIG. 17.

FIG. 18 illustrates an arrangement of an endoscope apparatus which effects display, as shown in FIG. 17.

An endoscope apparatus 151 shown in FIG. 18 comprises an electronic scope 153 having an elongated inserting section 152; an endoscope control apparatus (also referred to as a scope control apparatus) 157 which is provided with a connector receptacle for connection with a connector 155 installed at an end portion of a universal cord 154 of this electronic scope 153 and accommodates a signal processing means; an observation monitor 158 for displaying a video signal output from this scope control apparatus 157; a photographic apparatus 161 which is installed on a photographic monitor 159 which displays this video signal; and a keyboard 162 for inputting data to be displayed on these two monitors 158, 159.

The above-described electronic scope 153 is so arranged that a light guide 163 is inserted into an inserting section 152 and transmits illumination light supplied from a light source 164 disposed in the scope control apparatus 157 so as to issue the illumination light toward an object. An image of the illuminated object is formed as an endoscopic image on an imaging surface of a CCD 166 by means of an objective lens 165 disposed at a distal end portion of the inserting section 152. This CCD 166 photoelectrically converts the optical image formed on the imaging surface and outputs it as a video signal. After being amplified by a preamplifier 167, the output signal of this CCD 166 is input to a video processing circuit 169 through a signal cable 168 and is output as an RGB chrominance signal of the NTSC system. This chrominance signal is input to a superimposing circuit 171, where it is superposed on data concerning the endoscopic image input from the keyboard 162, and is displayed on the observation monitor 158 or the photographic monitor 159. Information as to whether or not the present status is a recording status is input to the superimposing circuit 171 by a VTR 172, and this information signal is also passed through the superimposing circuit 171 and is displayed on the monitors 158, 159 together with other data to be superimposed.

In this embodiment, the aforementioned light source 164 is of a type in which illumination is carried out consecutively by using color filters. Specifically, white light of the light source lamp 172, after passing through a rotary filter 174 rotatively driven by a motor 173, is condensed and radiated to an incident end of the light guide 163 by means of a condenser lens 175. The rotary filter 174 is provided with color filters for allowing the light of various wavelengths of red, green and blue to be transmitted therethrough, and the object is consecutively illuminated with the illumination light of red, green and blue which has consecutively passed through these color filters.

In this embodiment, an endoscopic image formed by using the CCD 166 is displayed on the monitor 159 (and the monitor 158) by being allowed to pass through the superimposing circuit 171.

A display screen 181 of this monitor 159 is of the NTSC system, and the aspect ratio of the screen is 3:4, while the photographing apparatus 161 for taking photographs by being mounted on this monitor 159 is so arranged as to an image on a film surface 184 of a 35 mm film 183 by means of an image-forming lens 182. As for the range of image formation in which an image is actually formed on this film surface 184, the aspect ratio is set to 2:3, which is different from the aspect ratio of 3:4 for the monitor screen 181.

For this reason, in this embodiment, a photographic range 185 in which photographs are taken with the photographing apparatus 161 mounted on the monitor 159 is displayed on the monitor screen 181 with a line, and the horizontal dimension of this photographic range 185 is set to the full horizontal dimension of the monitor screen 181, while the vertical dimension is set such as to be slightly smaller than that of the monitor screen 181.

Thus the arrangement is such that displayed within the photographic range 185 are an endoscopic image 186 formed by using the CCD 166 as well as data 187 concerning this endoscopic image 186 (e.g., a patient No. 188a, the name of patient 188b, the birth date of patient 188c, the name of the sickness 188d, the date of diagnosis 188e, the number of photographed frames and the remaining number of frames 188f, etc.).

Incidentally, although display is given as to whether or not the VTR 172 is in a recording status, i.e., a display 189 of VTR-ON or VTR-OFF is given on the monitor screen 181, this information is not necessary to be superimposed on the film, so that it is displayed outside the photographic range 185.

Figure 19:
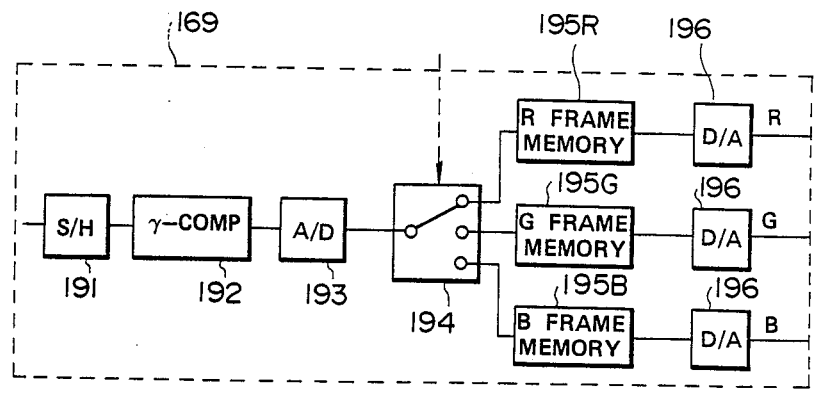
FIG. 19 is a schematic diagram illustrating the configuration of a video processing circuit shown in FIG. 18.

FIG. 19 illustrates a configuration of the video processing circuit 169 to which the output signal of the CCD 166 is input via the preamplifier 167.

Namely, the signal which is input via the preamplifier 167 is input to a sample-hold circuit 191, and is, after sample-holding, subjected to $\gamma$-compensation by a $\gamma$-compensating circuit 192, and is then converted into a digital amount by an A/D converter 193. Subsequently, after the digital signal goes through a multiplexer 194 which is changed over by a signal of a timing generator (not shown), the signals formed consecutively under the illumination through the R, G and B filters are written in an R frame memory 195R, a G frame memory 195G, and a B frame memory 195B. The signal data written in the respective frame memories 195R, 195G, and 195B are read simultaneously, and are converted into analog chrominance signals R, G and B by D/A converters 196, respectively, and are then input to the superimposing circuit 171. Subsequently, the signals are displayed on the monitors 158, 159 in color via the superimposing circuit 171.

Incidentally, the arrangement is such that the endoscopic image 186 and the data 187 displayed on the monitor 159 can be transmitted to the photographing apparatus via a release signal line 199 as a release switch 198 provided on the operating section of the electronic scope 153 is turned ON, thereby allowing a shutter to be released.

Figure 20:
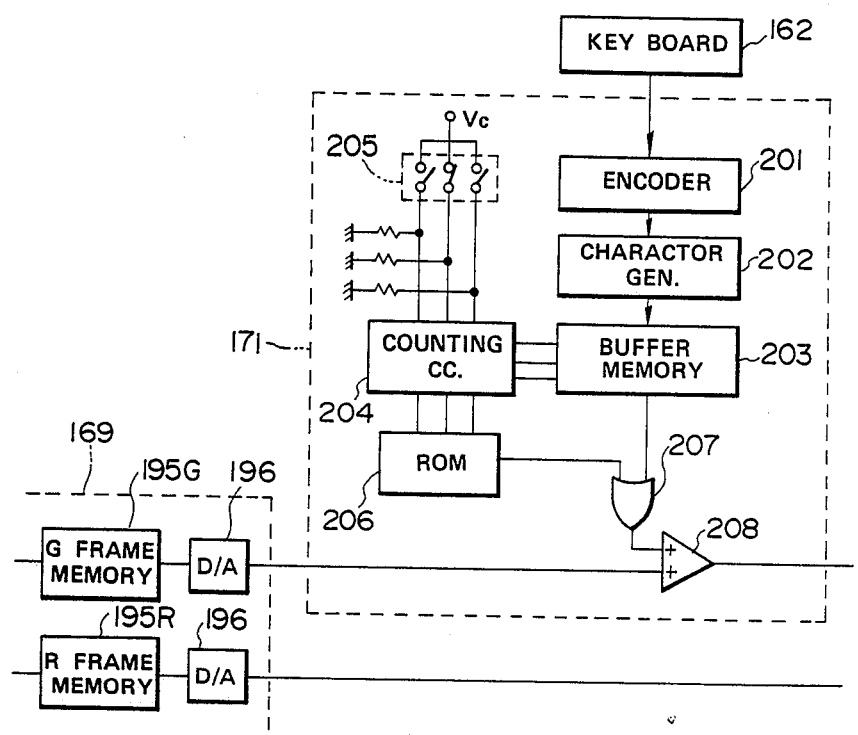
FIG. 20 is a schematic diagram illustrating the configuration of a superimposing circuit shown in FIG. 18.

The aforementioned superimposing circuit 171 has a configuration such as the one shown in FIG. 20.

A code signal corresponding to a key which has been depressed on the keyboard 162 is output from an encoder 201. A corresponding address signal is applied to a character generator 202, and character data such as a character defined by the address signal is read, and is transferred to a buffer memory 203. A read-out clock is applied to this buffer memory 203 from a counter circuit 204 for display. This clock ensures that a data font for forming character data is synchronized with horizontal synchronizing signals and vertical synchronizing signals.

In this case, the position of display of character data displayed is determined by data preset in the counter circuit 204, and this preset data is so arranged that it can be determined by, for instance, a dip switch 205. In this embodiment, the arrangement is provided such that display is given on the right-hand side of the photographic range 185 by means of this preset data.

In addition, this counter circuit 204 applies an address signal to a ROM 206 in which frame data for displaying the frame of the photographic range 185 is written, so as to read the frame data (rectangular frame data). This data as well as data output from the buffer memory 203 are output via an OR circuit 207. The output data of this OR circuit 207 is read from, for instance, the G memory 195G, and is then added to the analog chrominance signal G by an adder 208 so as to be displayed on the monitors 158, 159 in green.

Incidentally, in order to allow the endoscopic image 186 to be accommodated within the photographic grange 185, the clocks for reading the frame memories 195R, 195G and 195B may be adjusted, or, in the case of normal reading, a portion which slightly projects vertically from the photographic range 185 may be masked.

According to this embodiment, the frame of the photographic range 185 within which photographing can be effected within the screen 181 of the monitor 159 is displayed, and the endoscopic image 186 and the data 187 concerning this endoscopic image 186 are displayed within this photographic range 185. Therefore, where photographing is performed, it is possible to overcome the drawback of the superimposed data becoming eclipsed and prevent the endoscopic image from protruding from the photographic frame.

In this embodiment, since the horizontal dimension of the monitor screen 181 is smaller than 1.5-fold the vertical dimension thereof, the horizontal dimension of the photographic range 185 is made substantially equivalent to the horizontal dimension of the screen 181. In this case, the data is displayed with as large a size as possible within the photographic range 185 and in a space adjacent to the endoscopic image.

Figure 21:
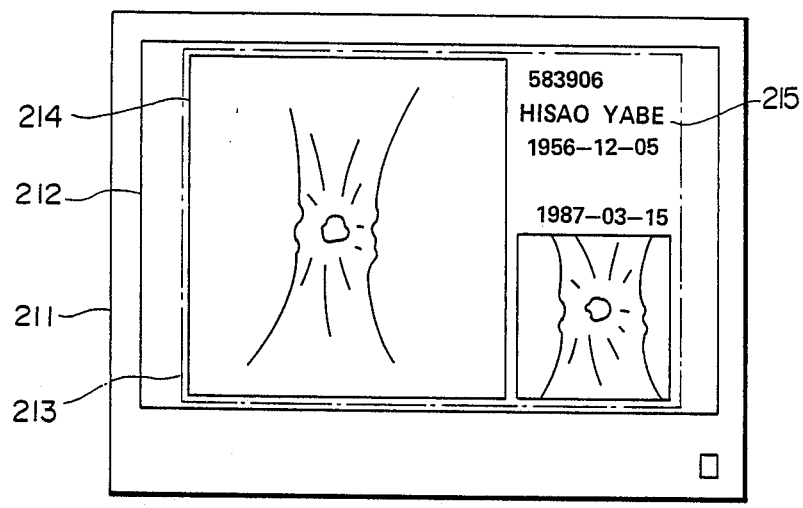
FIG. 21 is a diagram illustrating a manner in which an endoscopic image and data are displayed on a monitor screen having an aspect ratio which is different from that of the monitor shown in FIG. 17.

Although the foregoing embodiment is applicable to the NTSC system or the PAL system, when it is applied to the high-definition television system, the display may be effected as shown in FIG. 21.

In this embodiment, the aspect ratio of a monitor screen 212 of a high-definition television 211 is 3:5, and its horizontal dimension is greater than the aspect ratio of 2:3 in the photographic frame of the 35 mm film.

Accordingly, in this case, as shown in FIG. 21, the vertical dimension of a photographic range 213 is set to the full vertical length of a monitor screen 212, and the horizontal dimension is set to 1.5-fold that vertical dimension. Subsequently, an endoscopic image 214 and data 215 on the upper right-hand side of and adjacent to this image 214 are shown within this photographic range 213. Furthermore, a central portion of a hue-emphasized endoscopic image is displayed below the data 215.

Figure 22:
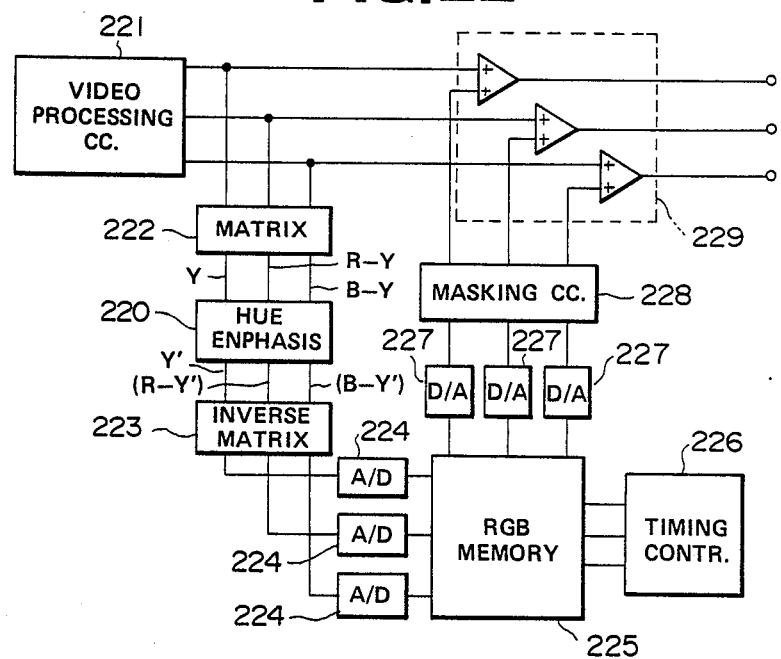
FIG. 22 is a schematic diagram of essential portions of a means for effecting the display shown in FIG. 21.

Incidentally, as shown in FIG. 22, signals which are obtained by converting R, G and B signals of a video processing circuit 221 into the luminance signal Y and the chrominance signals R - Y, B - Y via a matrix circuit 222 are input to a hue emphasis circuit 222 for effecting the aforementioned hue emphasis. As for this hue emphasis circuit, for example, one used in Japanese Utility Model Application No. 202,508/1986 may be used. The hue-emphasized signals are converted into R, G and B chrominance signals via an inverse matrix circuit 223 and are stored in an RGB memory 225 via A/D converters 224, respectively.

The signals stored in this RGB memory 225 are read by a read-out timing control circuit 226 at a timing with a time lag with that of the video processing circuit 221, are delivered via D/A converters 227 and a masking circuit 228 to a superimposing circuit 229 constituted by adders, and are then output to the high-definition television 211. Subsequently, only a part of the central portion this hue-emphasized image is disposed on the lower right-hand side of FIG. 21.

In this embodiment, since the horizontal dimension of the monitor screen is greater than 1.5-fold the vertical dimension, the vertical dimension of the photographic range is set such as to be substantially equivalent to the vertical dimension of the screen, and the photographic range is set by making the optimum use of the monitor screen. Accordingly, as compared with a conventional displaying method, there are practically no cases where the resolution declines.

Incidentally, in the case of the display shown in FIG. 17, since the data which need not be superimposed (e.g., VTR-ON and VTR-OFF) are displayed outside the photographic range, it is possible to superimpose only the necessary data for the film in a greater volume or with larger characters, or it is possible to superimpose them in a clear-cut manner.

In addition, an arrangement may be provided such that the display is effected automatically after converting the size of the character displaying portion on a reduced scale or the like in the endoscope control apparatus so that the data will be kept inside the photographic range.

Incidentally, although, in the foregoing embodiment, a description has been given of an example using the aspect ratio of the photographic range in the case of a 35 mm film, i.e., 2:3 (or 1:1.5), the present invention can similarly be applied with other aspect ratios.

In addition, the display of a frame portion for indicating the photographic range is not necessarily required in each of the foregoing embodiments.

Furthermore, in the present invention, it is possible to provide other different embodiments by partially combining the above-described embodiments.

What is claimed is:

1. An imaging apparatus comprising:
   illumination means including a light source lamp for generating illumination light, mechanical transmissive light quantity restricting means disposed at a forward position on an optical path of said light source lamp and adapted to restrict a quantity of transmissive light of said illumination light, and lamp radiation controlling means for controlling the radiation of said light source lamp;
   imaging means formed by using a solid-state imaging device;
   solid-state device driving means for outputting a drive signal so as to read a signal photoelectrically converted by said solid-state imaging device;
   signal processing means for generating a video signal of a predetermined system with respect to a signal read by said solid-state imaging device upon application of said drive signal thereto;
   imaging controlling means for substantially inhibiting imaging by said solid-state imaging device during a transient period of time until said transmissive light quantity restricting means reaches a predetermined amount of opening; and
   means for controlling said transmissive light quantity controlling means which is adapted to decrease an amount of opening of said transmissive light quantity controlling means in a predetermined imaging period after a time when said transmissive light quantity controlling means has reached said predetermined amount of opening.

2. An apparatus according to claim 1, wherein a luminance signal generated by said signal processing means is input to said lamp radiation controlling means, and driving electric power for said light source lamp is varied on the basis of the level of said luminance signal so as to control radiation power.

3. An apparatus according to claim 1, wherein said transmissive light quantity restricting means is constituted by a diaphragm whose aperture changes by the movement of a plurality of diaphragm blades.

4. An apparatus according to claim 1, wherein, if said solid-state imaging device is of a type which is capable of resetting a signal formed upon application of a reset signal, said imaging controlling means applies said reset signal at a timing when said predetermined amount of opening has been reached.

5. An apparatus according to claim 1, wherein said imaging controlling means is constituted by a liquid crystal shutter disposed in front of an imaging surface of said solid-state imaging device and a liquid crystal driving circuit for applying a potential for moving said liquid crystal shutter such as to render said liquid crystal shutter transmissive at a timing when said predetermined amount of opening has been reached.

6. An apparatus according to claim 1, wherein said imaging means is incorporated in an endoscope.

7. An apparatus according to claim 1, wherein said means for controlling said transmissive light quantity controlling means has means for variably setting said predetermined imaging period in correspondence with a distance to an object.

8. An apparatus according to claim 1, wherein said transmissive light quantity restricting means is formed by a rotary shutter which is constituted by a disk-shaped light-shielding plate rotatively driven by a motor and an opening formed by making a notch at a portion of an outer periphery of said light-shielding plate.

9. An apparatus according to claim 8, wherein there is provided means for moving said rotary shutter away from an optical path of said illumination light.

10. An apparatus according to claim 1, wherein said signal processing means has memory means for storing signal data of a number of pixels corresponding to at least one field of said solid-state imaging device.

11. An apparatus according to claim 10, wherein said memory means is capable of storing signal data of a number of pixels corresponding to two fields of said solid-state imaging device.

12. An apparatus according to claim 1, wherein said driving means is adapted to output a drive signal after an elapse of said predetermined imaging period.

13. An apparatus according to claim 12, wherein said driving means is further adapted to output a drive signal at a timing corresponding to one half said predetermined imaging period.

* * * * *